(12) United States Patent
Onozato

(10) Patent No.: US 8,563,804 B2
(45) Date of Patent: Oct. 22, 2013

(54) AMPHIDIPLOID AQUATIC ANIMAL AND METHOD OF BREEDING THE SAME

(75) Inventor: Hiroshi Onozato, Azumino (JP)

(73) Assignees: Matsumoto Institute of Microorganisms Co., Ltd., Matsumoto-shi (JP); Light Black, Inc., Tokyo (JP)

( * ) Notice: Subject to any disclaimer, the term of this patent is extended or adjusted under 35 U.S.C. 154(b) by 356 days.

(21) Appl. No.: 12/841,114

(22) Filed: Jul. 21, 2010

(65) Prior Publication Data

US 2010/0313819 A1 Dec. 16, 2010

Related U.S. Application Data

(63) Continuation of application No. 11/663,851, filed as application No. PCT/JP2004/014760 on Sep. 29, 2004, now abandoned.

(51) Int. Cl.
*A01K 67/027* (2006.01)
*C12N 15/00* (2006.01)

(52) U.S. Cl.
USPC .............................................. 800/20; 800/21

(58) Field of Classification Search
USPC ...................................... 800/20, 21; 119/215
See application file for complete search history.

(56) References Cited

U.S. PATENT DOCUMENTS 5,824,841 A 10/1998 Guo et al.

FOREIGN PATENT DOCUMENTS

| JP | A 10-501401 | 2/1998 |
|---|---|---|
| JP | A 10-150883 | 6/1998 |
| JP | A 10-327706 | 12/1998 |

OTHER PUBLICATIONS

Nakada et al., 1991, Hokkaido University Collection of Scholarly and Academic Papers, pp. 356-364.*
May 17, 2012 Notice of Rejection issued in Taiwanese Patent Application No. 95105896 with English-language translation.
Jul. 31, 2012 Office Action issued in Korean Office Action No. 10-2007-7009565 with English-language translation.
Nov. 29, 2011 Korean Office Action issued in Korean Application No. 10-2007-7009565 with English-language translation.
Oct. 17, 2011 Office Action issued in Taiwanese Patent Application No. 95105896 (with translation).
Kawamura et al., "Allopentaploids and Allohexaploids between *Rana nigromaculata* and *Rana plancyi chosenica*," Sci. Rep. Lab. Amphibian Biol., Hiroshima Univ., vol. 11, pp. 161-195, 1992.
Sep. 7, 2010 Notification of Reasons for Rejection issued in Japanese Application No. 2006-537611 with English translation.
X. Guo et al., "Viable Tetraploids in the Pacific Oyster (*Crassostrea gigas* Thunberg) Produced by Inhibiting Polar Body 1 in Eggs from Triploids", Molecular Marine Biology and Biotechnology, vol. 3, No. 1, 1994, pp. 42-50.
J. Kurita et al., "Production of Amphidiploid Medaka *Oryzios 2 latipes sinesis-2 curvinotus* by Gynogenesis with Retention of the Second Polar Body", Nippon Suisan Gakkaishi, vol. 59, No. 2, 1993, p. 373.
T. Nakada, "Cocoon Weight of Polyploids Originated in the Crossing of Some Gene Marker Strains in the Silkworm, *Bombyx mori* L.", Hokkaido University Nogakubu Hobun Kiyo, vol. 17, No. 3, 1991, pp. 356-364.
F. Li et al., "Optimization of Triploid Induction by Heat Shock in Chinese Shrimp *Fenneropenaeus chinesis*", Aquculture, vol. 219, 2003, pp. 221-231.
H. F. Ma et al., "Fertility of Hybrids Between Female Masu Salmon, *Oncorhynchus masou* and Male Pink Salmon, *O. gorbuscha*", Bull. Fac. Fish. Hokkaido Univ., vol. 37, No. 4, 1986, pp. 295-302.
"Chromosome Manipulation and its Application for Aquaculture", Nippon Suisan Gakkai, 1989, pp. 87-94.
Chourrout et al., "Production of Second Generation Triploid and Tetraploid Rainbow Trout by Mating Tetraploid Males and Diploid Females—Potential of Tetraploid Fish," Theoretical and Applied Genetics, vol. 72, No. 2, pp. 193-206, Mar. 1986.

\* cited by examiner

*Primary Examiner* — Maria Leavitt
(74) *Attorney, Agent, or Firm* — Oliff & Berridge, PLC

(57) ABSTRACT

An amphidiploid aquatic animal according to the present invention has genomes AB of different species and carries fertile XXXY sex chromosomes. Among a large number of aquatic animals of the first filial generation kept in a closed system, a nonreductive sperm of a male and a nonreductive egg of a female are selected. Then the nonreductive egg is fertilized with the nonreductive sperm to create an amphidiploid aquatic animal having fertile XXXY sex chromosomes. Since this amphidiploid has the XXXY sex chromosomes, it can be crossed with an egg $A_XB_X$ of an F1 hybrid that produces nonreductive eggs, thus ensuring a stable creation of amphidiploids in the subsequent generations by natural crossbreeding. In the meiotic division, one set of the chromosomes of each species is assuredly distributed to each gamete. Therefore, the trait of the first generation (F1) will be perpetually maintained. Since no genetic separation takes place, two sets of the genomes of different species are always inherited to every individual. Therefore, inbreeding depression will not take effect even if relative mating is repeated.

1 Claim, 11 Drawing Sheets

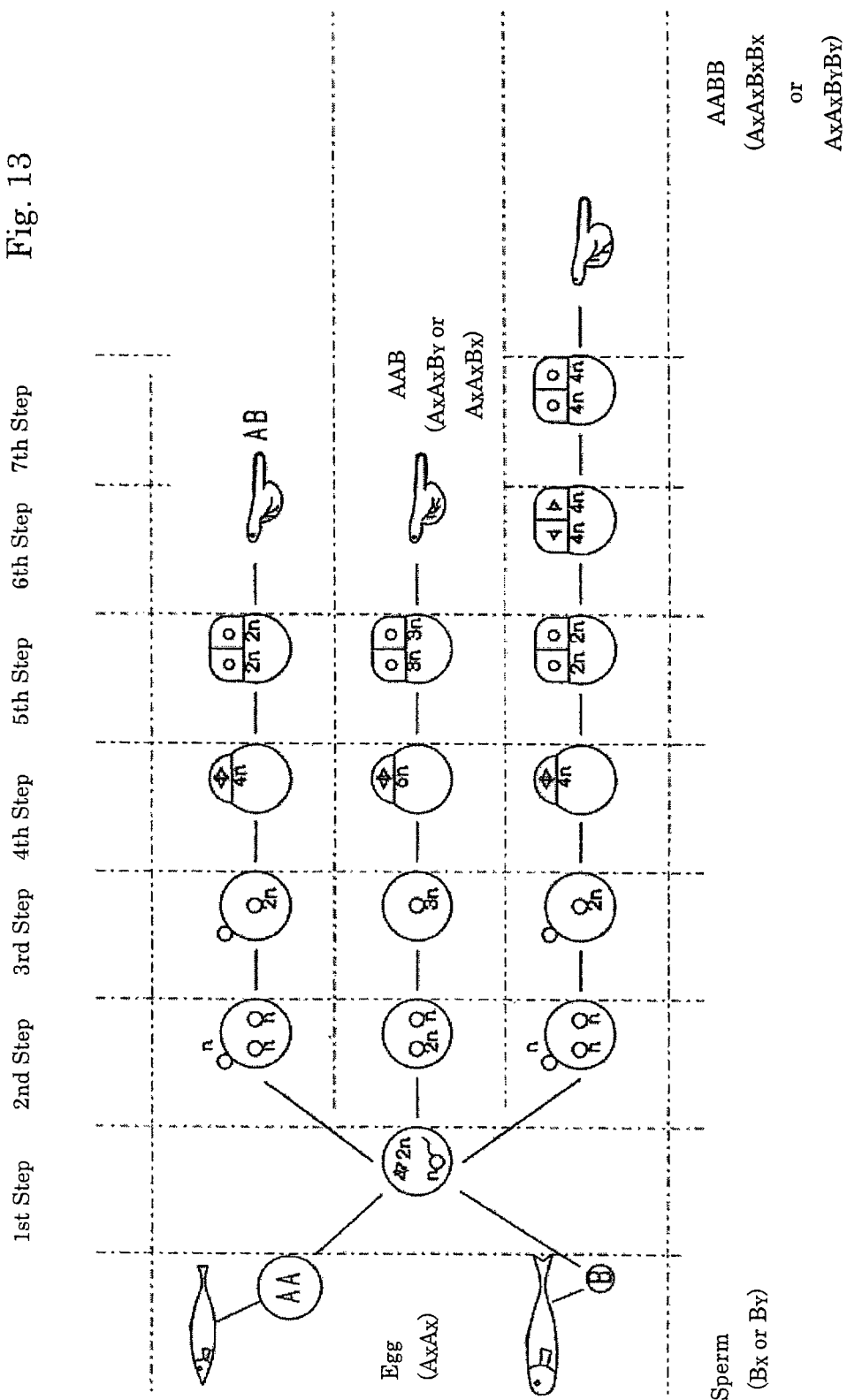

US 8,563,804 B2

AMPHIDIPLOID AQUATIC ANIMAL AND METHOD OF BREEDING THE SAME

This is a Continuation of application Ser. No. 11/663,851 filed Mar. 27, 2007, now abandoned, which is a National Stage Application of PCT/JP2004/014760 filed Sep. 29, 2004. The entire disclosures of the prior applications are hereby incorporated by reference in their entirety.

TECHNICAL FIELD

The present invention relates to an amphidiploid of aquatic animals, such as fish, shellfish and Crustacea, and a method of breeding such animals. Particularly, the present invention relates to an amphidiploid aquatic animal that can be created in a stable manner without causing genetic separation in the subsequent hybrid generations.

BACKGROUND ART

In the process of creating a species cross or genus cross of fish or other aquatic animals, embryogenesis begins with the fertilization of an egg. However, most hybrids thereby created will be finally dead, and—those hybrids which remain alive will be sterile due to pairing failure, which results from the nonhomogenity of their chromosomes. Crossing between allied species can make the pairing successful and provide them with fertility. However, the next generation would suffer from genetic separation, so that their qualities superior to those of the parents (i.e. the hybrid vigor) will be gradually lost, generation by generation.

FIGS. 11 and 12 schematically show genomic combinations in the creation of the aforementioned hybrids and in the crossing among the members of the first filial generation. It should be noted that the Claims and Description sections and the drawings of the present patent application use the following notations: Genomes (or chromosomes) of different species (A and B) are generally referred to as "A" and "B", respectively. Sex chromosomes are denoted by "X" and "Y." If a genome of species A or B needs to have its sex chromosome explicitly indicated, the chromosome of species A is referred to as "$A_X$" or "$A_Y$" and the chromosome of species B as "$B_X$" or "$B_Y$." In the case where an individual of a fish having genomes AA has laid an egg, the egg retains the second polar body immediately before fertilization. Therefore, this egg is referred to as AA even if it is a reductive egg. The egg will be a real reductive egg (A) for the first time after it has released the second polar body subsequent to its fertilization. Accordingly, a reductive egg is regarded as "A" even if it is an unfertilized egg, except when the second polar body is retained.

In FIG. 11, the chromosome constitution of the first filial generation is either $A_X B_X$ or $A_X B_Y$. These combinations may be lethal or sterile, as explained earlier, depending on the constitution of genome A on the maternal side and genome B of the paternal side. Some hybrids may keep living and be fertilized, but they will undergo genetic separation, as shown in FIG. 12. For example, let the chromosomes constituting the genomes A and B of an F1 hybrid (AB) denoted by a1, a2 and a3 and b1, b2 and b3, respectively. Provided that the meiotic division normally takes place, the resultant gamete will have eight possible chromosome combinations, including a1 or b1 as the first chromosome, a2 or b2 as the second chromosome, and a3 or b3 as the third chromosome. Therefore, the F2 hybrids will have 64 possible combinations, some of which have two chromosomes of the same kind combined for each of the first through third chromosomes, such as a1a1 or a3a3. In the most extreme case, the resultant combination can consist of only the chromosomes of species A: a1a1a2a2a3a3. Thus, the qualities of the hybrids are separated into species A or B at each chromosome (or at each gene, if a crossover is taken into account).

It is generally believed that the lethality of the species hybrid or genus hybrid can be avoided by polyploidizing the chromosomes, although its effect depends on the combination of the parent species. Polyploidization, particularly the polyploidization resulting from the prevention of somatic division, is practically used for a variety of plants but barely used for animals.

With respect to the techniques for creating an autotriploid in the field of aquatic animals, particularly fish, there are two patent documents disclosing such techniques relating to sweetfish and flatfish (Unexamined Japanese Patent Application Publication Nos. H10-150883 and H10-327706. The former is called "Patent Document 1" and the latter "Patent Document 2" hereinafter). Concerning the creation of an allotriploid or allotetraploid (which is called the "amphidiploid" hereinafter), there is a report on the successful creation of an allotriploid of salmon (for example refer to Nippon Suisan Gakkai ed. 1989. Suisan Zouyoushoku To Senshokutai Sousa. Tokyo: Kouseisha-kouseikaku. pp. 87-92. This document is called "Non-Patent Document 1" hereinafter). However, concerning amphidiploids, the techniques proposed thus far are only theoretical, general ones except for some unusual cases (see Non-Patent Document 1). Neither has there been any report on the existence of an amphidiploid of a dioecious aquatic animal in the natural world, as opposed to plants, which are capable of self-fertilization.

With reference to FIG. 13, a technique of creating an allotriploid and an amphidiploid of a fish is outlined. FIG. 13 and the technique described below are based on FIG. 8-2 and its description in Non-Patent Document 1.

To create an allotriploid, an egg of species A (an egg in the middle of the second maturation division, with chromosomes $A_X A_X$) is fertilized with a sperm of species B (chromosome $B_X$ or $B_Y$) (the first step in FIG. 13). Then, the egg is subjected to a temperature or pressure to suppress the release of the second polar body (the second step). With the second polar body thus retained, the egg now has a triploid chromosome constitution (AAB) (the third through fifth steps). Therefore, the fish finally obtained will be an allotriploid ($A_X A_X B_X$ or $A_X A_X B_Y$).

To create an allotetraploid (i.e. amphidiploid), an egg of species A is fertilized with a sperm of species B. Then, without suppressing the release of the second polar body, the first cleavage is prevented or suppressed in the fifth step (it should be noted that, according to a study of the present inventor, what is actually suppressed hereby is not the first cleavage but the second one, as will be explained later). The egg thus obtained has a tetraploid chromosome constitution (AABB). Therefore, the fish finally obtained will be an amphidiploid.

In a specific example of the creation of an amphidiploid, *Oryzias luzonensis* was crossed with *Oryzias curvino* (Nippon Suisan Gakkaishi, 1993, 59: 373. This document is called "Non-Patent Document 2" hereinafter). This technique is not a mere replication of the method disclosed in Non-Patent Document 1; it further includes the step of inseminating a nonreductive egg $A_X B_X$ ($A_X A_X B_X B_X$ before the release of the polar body) of a cross breed with a sperm genetically inactivated by an irradiation of gamma ray, ultraviolet ray, X-ray or similar radiation. This treatment prevents the second maturation cleavage of the inseminated egg; thereby causing the egg to be an amphidiploid.

The amphidiploid thus created has $A_X A_X B_X B_X$ chromosomes. The sister chromosomes function like homologous chromosomes, so that the fertility is restored. As long as the gynogenesis using the eggs produced by this amphidiploid is continued, the progeny individuals will be genetically identical and no male will appear.

The allotriploid mentioned earlier can solve the problem of lethality of the species hybrid or genus hybrid. However, since its chromosome constitution is $A_X A_X B_X$ or $A_X A_X B_Y$, the allotriploid will usually be sterile due to pairing failure of the chromosomes during the meiotic division. Therefore, every time a species hybrid of a specific kind is demanded, it is necessary to repeat the previously described treatment. This means that this technique of creating an allotriploid does not enable the progenies to be produced by natural crossbreeding. This fact restricts the application of this technique in the field of aquaculture and propagation.

Amphidiploids of aquatic animals are said to be theoretically possible. However, there has been only one successful case, as explained earlier. Since that successful case is a kind of gynogenesis, the individuals thereby created are all female ($A_X A_X B_X B_X$). The amphidiploid created in the theoretical example shown in FIG. 13 will be either a female having $A_X A_X B_X B_X$ chromosomes or a male having $A_X A_X B_Y B_Y$ chromosomes. However, there has not been any report on a successful creation of an amphidiploid by this theoretical technique. Thus, currently, there is no evidence that a male amphidiploid actually exists. Moreover, the theory predicts only the possibility of $A_X A_X B_Y B_Y$.

For the reasons described above, amphidiploids are technically more difficult to use in the aquaculture and propagation of aquatic animals than allotriploids.

Thus, the present invention intends to provide an amphidiploid aquatic animal and a method of breeding such an animal, which have the following features: the hybrids are free from lethality and sterility; the hybrid vigor is maintained also in the progeny; the subsequent generations can be created by normal crossing in a stable manner; and the inbreeding depression due to relative mating is totally eliminated.

DISCLOSURE OF THE INVENTION

To achieve the above objective, the present invention provides various amphidiploid aquatic animals as follows:

Firstly, the present invention provides an amphidiploid aquatic animal having genomes AB of different species, which carries fertile XXXY sex chromosomes.

The present invention can be used for not only fish but also aquatic animals in general, including shellfish and Crustacea. It can be particularly applicable to aquatic animals whose seedlings are produced for the purpose of releasing or breeding. For example, the present invention is applicable to species hybrids or genus hybrids of the following animals: flatfish, sea bream, tuna, yellowtail, trout, carp, lobster, prawn, shrimp, crab, abalone, oyster, pearl oyster, clam, asari clam, sea urchin and sea cucumber. The species or genus combinations are not limited to those animals that can be crossed with each other; even a lethal combination is acceptable if its survivability can be restored by polyploidization.

An amphidiploid having $A_X A_X B_X B_Y$ chromosomes has not been found in the real world or predicted in literature. Having created this novel creature, the present inventor proposes it as an industrially beneficial species. The fertility of the species depends on whether or not it produces gametes that can be fertilized and then smoothly develop through the subsequent stages. The present invention accepts any possible method or process to create the amphidiploid.

The present invention further provides an amphidiploid aquatic animal having fertile XXXY sex chromosomes, created by fertilizing a nonreductive egg of a female of the first filial generation of an aquatic animal having genomes AB of different species with a nonreductive sperm of a male of the first filial generation of the aquatic animal having the same genomes AB. FIG. 1 schematically shows the process of creating this amphidiploid.

A nonreductive sperm is a sperm having the same chromosome constitution as that of the parent individual. For example, suppose that a male having chromosomes $A_X B_Y$ produces a reductive sperm. In this case, the spermatogonium having an $A_X B_Y$ chromosome constitution usually undergoes polyploidization and two rounds of divisions, so that its chromosome constitution is either $(A+B)/2_X$ or $(A+B)/2_Y$ at the moment of fertilization. In contrast, the nonreductive sperm is produced without such polyploidization and division processes, so that it retains the chromosome constitution of the parent individual, $A_X B_Y$, at the moment of fertilization.

A nonreductive egg is an egg having the same chromosome constitution as that of the parent at the moment of fertilization (i.e. when it releases the second polar body). For example, a female having chromosomes $A_X B_X$ produces an oogonium having chromosomes $A_X B_X$. This oogonium usually undergoes doubling and releases the polar body twice, so that its chromosome constitution is $(A+B)/2_X$ at the moment of fertilization. In contrast, the nonreductive egg is produced without such doubling and polar-body releasing processes, so that it eventually retains the chromosome constitution of the parent, $A_X B_X$.

Fertilizing the nonreductive egg $A_X B_X$ of the first filial generation with the nonreductive sperm $A_X B_Y$ of the first filial generation produces a fertilized egg having an $A_X A_X B_X B_Y$ chromosome constitution. All the individuals finally produced will be male amphidiploids having an $A_X A_X B_X B_Y$ chromosome constitution.

A large number of aquatic animals of the first filial generation are kept in a closed system until they reach a maturation age. Then, during the spawning season, the abdomen of a male individual is pressed to check whether or not an ejaculation takes place and the DNA content of the sperm is measured to check that the sperm is a nonreductive one. This male is kept in an aquarium with a female to induce oviposition. Then, the DNA content per cell nucleus of a child fish thereby produced is measured, and if the child is a tetraploid, it is highly probable that the child is an amphidiploid. The male parent that has produced the nonreductive sperm can be repeatedly used as the parent also in the following years. It is possible to check the polyploidy of a child produced by oviposition within a closed system on the basis of the DNA content and size of the cell nucleus; if the child is a tetraploid, it means that both the egg and the sperm involved in the fertilization were nonreductive gametes. The parents involved in the oviposition are separated from the other individuals. Thus, the parents that produce nonreductive gametes can be selected.

The present invention provides another amphidiploid aquatic animal having fertile XXXY sex chromosomes, created by fertilizing a reductive egg with a reductive sperm, both produced by the first generation of an amphidiploid aquatic animal having XXXX or XXYY chromosomes obtained by suppressing the second cleavage of a cross egg produced between an aquatic animal of species A having genomes AA with another aquatic animal of species B having genomes BB.

This amphidiploid is created as the second generation by the steps of creating an amphidiploid as the first generation and then fertilizing its reductive egg with its reductive sperm. FIG. 2 schematically shows this process.

The suppression of the second cleavage carried out during the creation of the amphidiploid of the first generation corresponds to a polyploidization mechanism that has been mistakenly recognized thus far as the suppression of the first cleavage. This process will be detailed in the second example of this patent application. All the amphidiploids created by the above process will have XXXY sex chromosomes.

The present invention also provides another amphidiploid aquatic animal having fertile $A_XA_XB_XB_Y$ chromosomes, created by the steps of creating an autotetraploid of an aquatic animal of species B having genomes BB, then fertilizing an egg of an aquatic animal of species A having genomes AA with the sperm of the aforementioned autotetraploid, and suppressing the release of the second polar body. FIG. 3 schematically shows the process of creating this amphidiploid.

The autotetraploid of an aquatic animal of species B having genomes BB can be created by a commonly known method. It should be noted that the suppression of cleavage of the fertilized egg in the creation of this autotetraploid is also the suppression of the second cleavage. Its mechanism will be detailed in the second example.

The amphidiploid produced by the present creation process has either $A_XA_XB_XB_X$ or $A_XA_XB_XB_Y$ chromosomes, as shown in FIG. 3. The one having $A_XA_XB_XB_Y$ chromosomes corresponds to the amphidiploid according to the present invention.

The present invention also provides another amphidiploid aquatic animal having fertile XXXY sex chromosomes, created by fertilizing a nonreductive egg $A_XA_XB_X$ of a fertile allotriploid of an aquatic animal having genomes AAB with a reductive sperm $B_Y$ of an aquatic animal having genomes BB.

Normally, an allotriploid is not fertile. The present invention is an amphidiploid created by using a nonreductive egg of a fertile allotriploid. FIG. 4 schematically shows the process of creating this amphidiploid.

The meaning of the "nonreductive egg" and the method of selecting such eggs are the same as in the invention of claim 2.

To suppress the release of the second polar body during the creation of the allotriploid, conventional techniques using pressure or heat are available.

The present invention also provides another amphidiploid aquatic animal having fertile XXXY sex chromosomes, created by the steps of fertilizing an egg $A_XA_X$ of an aquatic animal having genomes AA before the egg releases the second polar body with a sperm $B_X$ or $B_Y$ of an aquatic animal having genomes BB, then suppressing the release of the second polar body, and fertilizing the egg with the sperm $B_Y$ or $B_X$ by microinjection, respectively.

This amphidiploid is characterized in that the sperm is directly injected into the egg by microinjection.

The present invention also provides another amphidiploid aquatic animal having fertile XXXY sex chromosomes, created by fertilizing an egg $A_XA_X$ with a sperm $B_XB_Y$, each produced by autotetraploids of species A and B (AAAA and BBBB).

This amphidiploid is characterized in that it is created from an egg and a sperm of autotetraploids strains created in advance.

A breeding method according to the present invention is characterized by the steps of selecting a nonreductive sperm of a male and a nonreductive egg of a female from a large number of aquatic animals of the first filial generation kept in a closed system and then fertilizing the selected nonreductive egg with the selected sperm to create an amphidiploid aquatic animal having fertile XXXY sex chromosomes.

Another breeding method according to the present invention is characterized in that it creates a male amphidiploid having $A_XA_XB_XB_Y$ chromosomes and a female amphidiploid having $A_XA_XB_XB_X$ chromosomes by a ratio of 1:1, by fertilizing reductive eggs $A_XB_X$ produced by an amphidiploid aquatic animal having $A_XA_XB_XB_X$ chromosomes with a sperm $A_XB_X$ or $A_XB_Y$ of an amphidiploid aquatic animal having $A_XA_XB_XB_Y$ chromosomes.

The present method uses an amphidiploid having $A_XA_XB_XB_Y$ chromosomes to create an amphidiploid having $A_XA_XB_XB_X$ chromosomes and an amphidiploid having $A_XA_XB_XB_Y$ chromosomes by a ratio of 1:1 in the F3 or subsequent generations. FIG. 5 shows the creation process according to this method.

The present method demonstrates that, if an amphidiploid having XXXY sex chromosomes is available, it is possible to create males and females of the amphidiploid by a ratio of 1:1 in the next and subsequent generations.

The amphidiploid according to the present invention has two sets of chromosomes of each of the two species constituting AABB. Fertility will recover because pairing becomes possible between homologous chromosomes of each species.

This amphidiploid has XXXY sex chromosomes and can be crossed with an egg $A_XB_X$ of an F1 hybrid that produces a nonreductive egg. Therefore, the next generation of the amphidiploid can be created in a stable manner by natural crossbreeding.

In the meiotic division, one set of the chromosomes of each species is assuredly distributed to each gamete. Therefore, the trait of the first generation will be perpetually maintained.

Since no genetic separation takes place, two sets of the genomes of different species are always inherited to every individual. Therefore, inbreeding depression will not take effect even if relative mating is repeated.

BRIEF DESCRIPTION OF THE DRAWINGS

FIG. 13 is a diagram showing a theoretical technique for creating an allotriploid and an amphidiploid by a conventional method.

BEST MODES FOR CARRYING OUT THE INVENTION

First Example

Amphidiploid between Goldfish and Colored Carp

Figure 1:
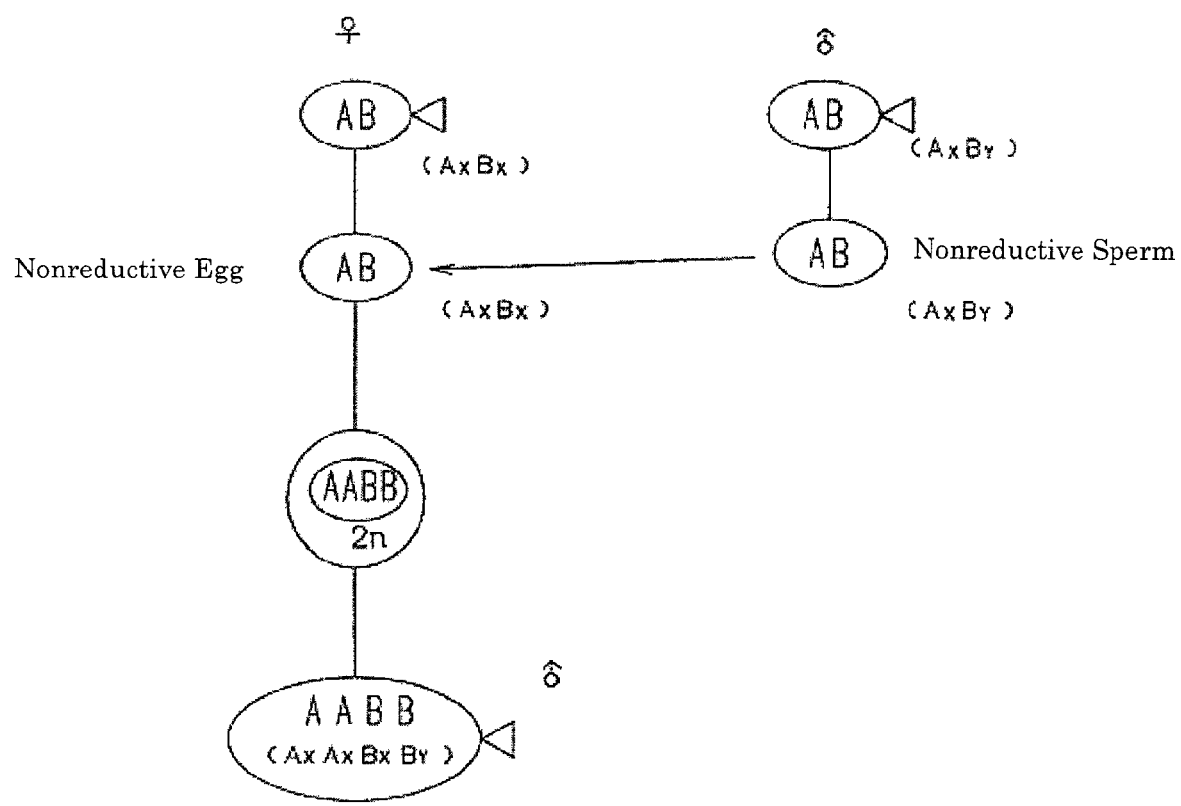
FIG. 1 is a diagram showing the process of creating an amphidiploid according to an example of the present invention.
Figure 2:
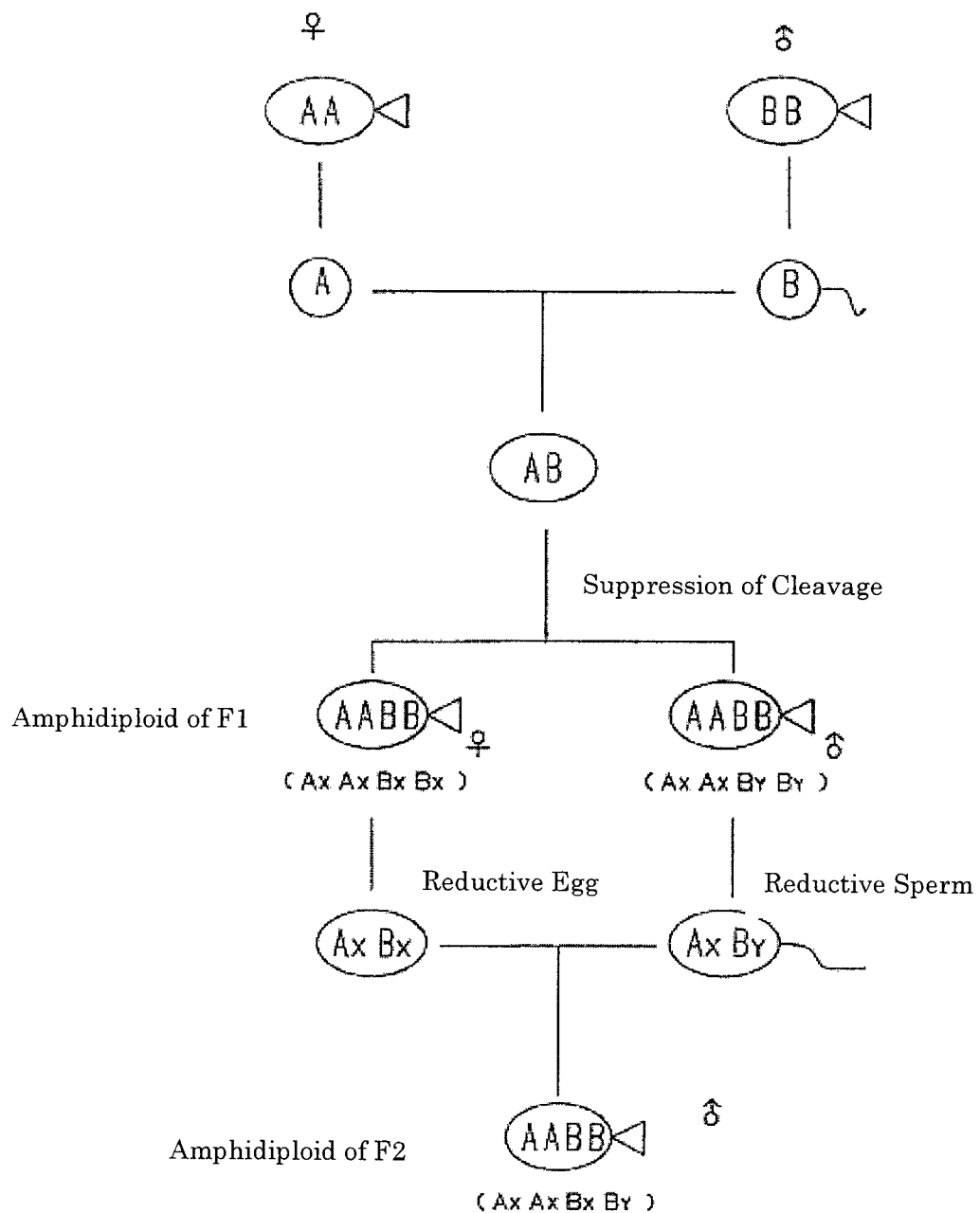
FIG. 2 is a diagram showing the process of creating an amphidiploid according to another example of the present invention.
Figure 3:
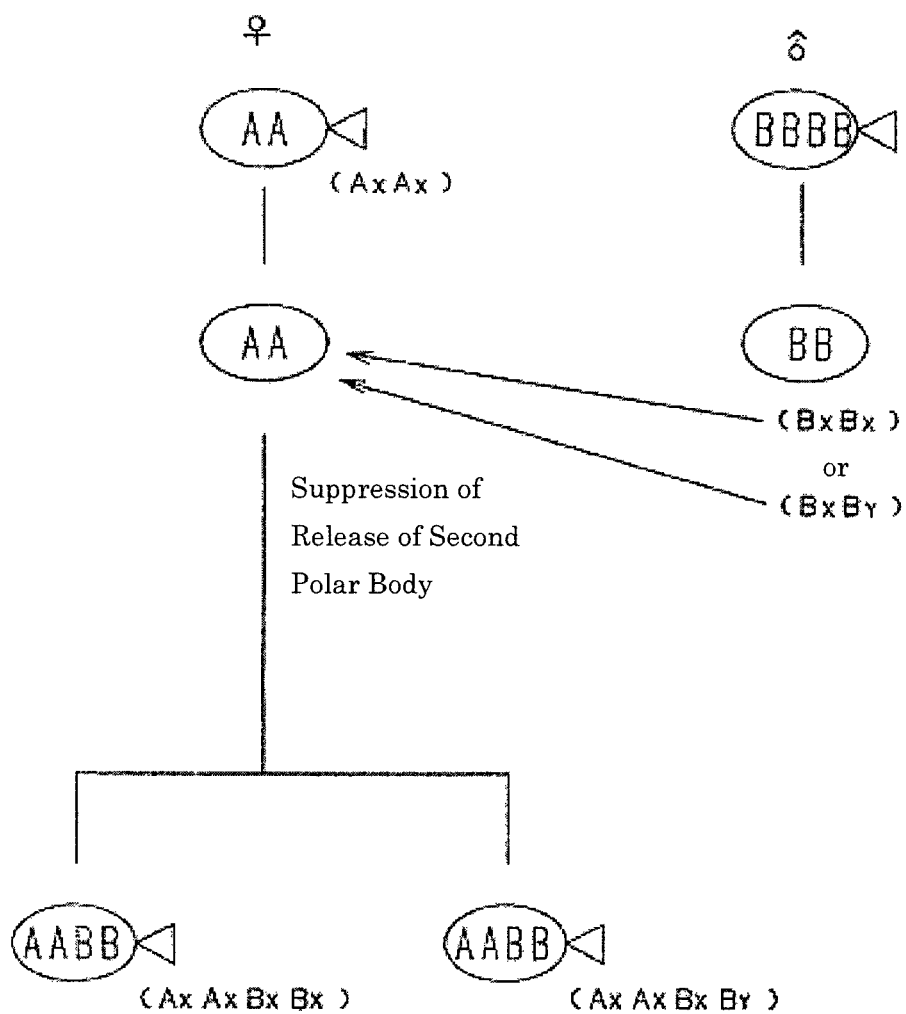
FIG. 3 is a diagram showing the process of creating an amphidiploid according to another example of the present invention.
Figure 4:
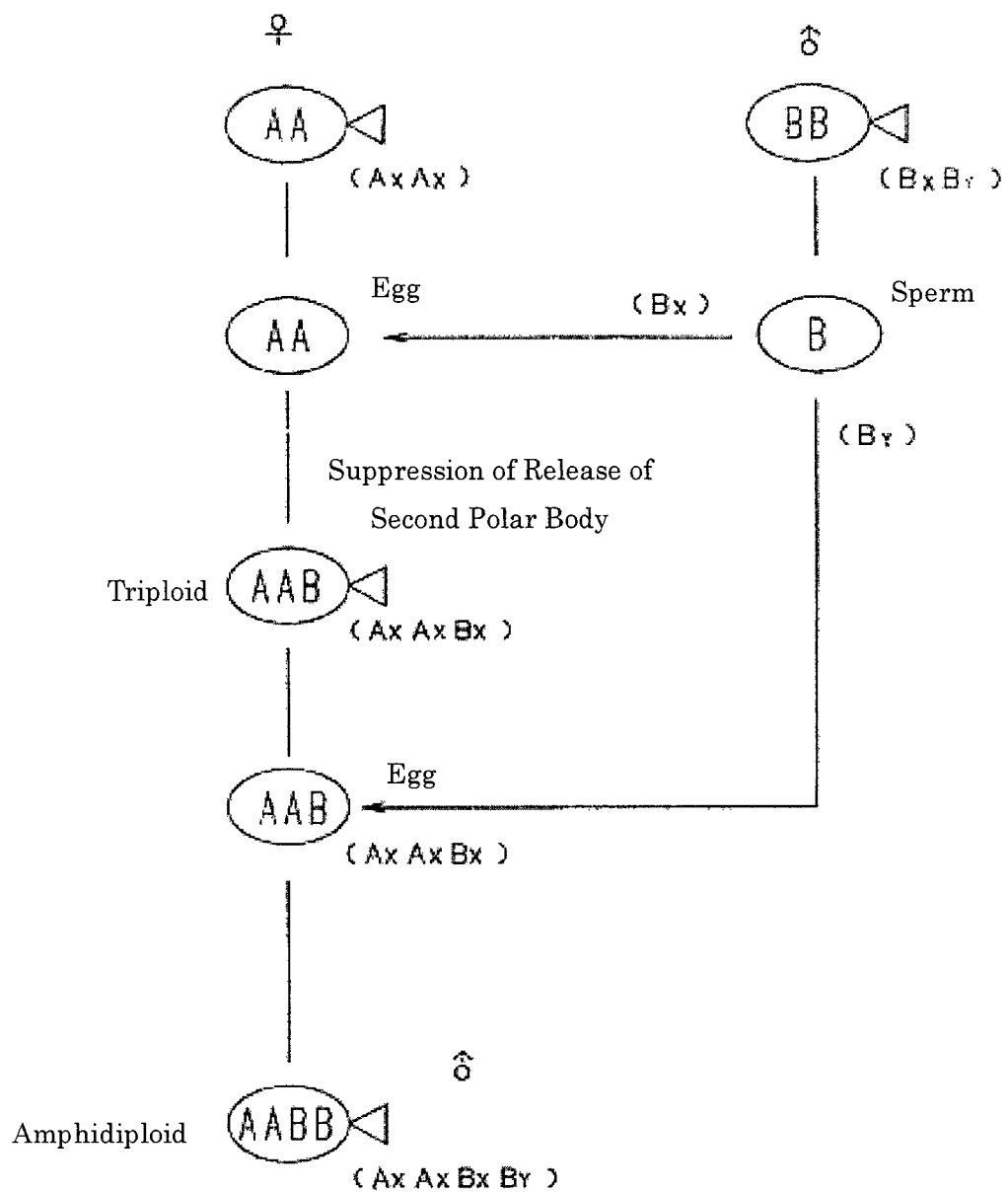
FIG. 4 is a diagram showing the process of creating an amphidiploid according to another example of the present invention.
Figure 5:
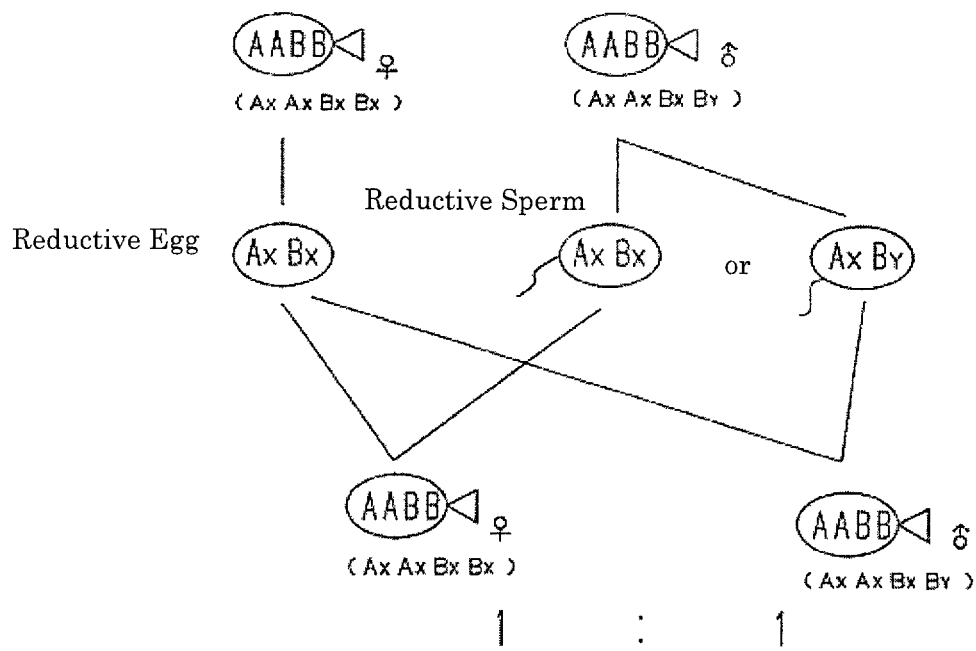
FIG. 5 is a diagram showing the process of a breeding method according to the present invention.

The present inventor has successfully created an amphidiploid fish having fertile XXXY sex chromosomes by crossing a female of colored carp (*Cyprinus carpio*) and a male of goldfish (*Carassius auratus*).

Background:

Colored carp has a wide variety of colors, such as gold and silver, which goldfish do not have. Accordingly, new kinds of goldfish having the colorfulness of the colored carp have been long desired. Since goldfish and carp are in intergeneric relationship to each other, their hybrids cannot produce normal gametes. However, female hybrids occasionally produce a nonreductive egg, which maintains the original chromosome number. In contrast, it has been believed that male hybrids cannot produce a nonreductive sperm. However, a study of a large number of F1 hybrids has revealed that some of them can produce a nonreductive sperm.

All the seven females studied produced nonreductive eggs, and all the fifteen males studied were found sterile. Then, another male individual that was accidentally involved in the oviposition was checked and found to be capable of producing a nonreductive sperm. These results suggest that female hybrids between goldfish and carp constantly produce nonreductive eggs while male hybrids producing nonreductive sperm are rare.

Method:

A comet or Wakin and a common carp or colored carp were crossed with each other. Six month later, their sexual glands were enucleated to histologically check whether gametes had been created. About three years later, the gonads of seven individuals were enucleated to check the gonad somatic index (GSI) and the state of the gametes created. For those individuals that had normally developed, the relative DNA content per one sperm of their parent and per blood cell of the children were measured. After one more year, the children underwent a sex check. Furthermore, the genetic relationship among the children was studied by scale transplantation and DNA fingerprint analysis.

Result:

The sexual glands of the six-month hybrids were undoubtedly abnormal compared with the control group. In the ovaries of the females, none or only a small number of oocytes in the diplotene stage were found. In the males, all the reproductive cells remained in the stage of spermatogonium and none of them was found to be in the meiotic division stage.

In contrast, among the approximately three-year old hybrids, four female and three male individuals were found to have normal sexual glands. The GSI values of the females ranged from 7.2 to 10.0 and those of the males from 0.9 to 2.9.

TABLE 1

Sexual glands of hybrids between goldfish and carp

| Individual No. | Sex | Body length (cm) | Weight (g) | Gland weight (g) | GSI (%) |
|---|---|---|---|---|---|
| 1 | Female | 35.0 | 651.9 | 51.9 | 9.8 |
| 2 | Female | 35.5 | 738.2 | 67.9 | 9.2 |
| 3 | Male | 31.5 | 374.9 | 3.5 | 0.9 |
| 4 | Female | 25.3 | 291.1 | 30.2 | 10.0 |
| 5 | Male | 21.4 | 148.0 | 2.3 | 1.5 |
| 6 | Male | 14.5 | 49.7 | 1.4 | 2.9 |
| 7 | Female | 25.7 | 302.5 | 21.9 | 7.2 |

All the eggs in the ovaries were well developed and all the female individuals were regarded as capable of oviposition. In contrast, none of the male individuals could ejaculate; no sperm was found even by microscopic examination. Accordingly, the males were determined as sterile.

Figure 6:
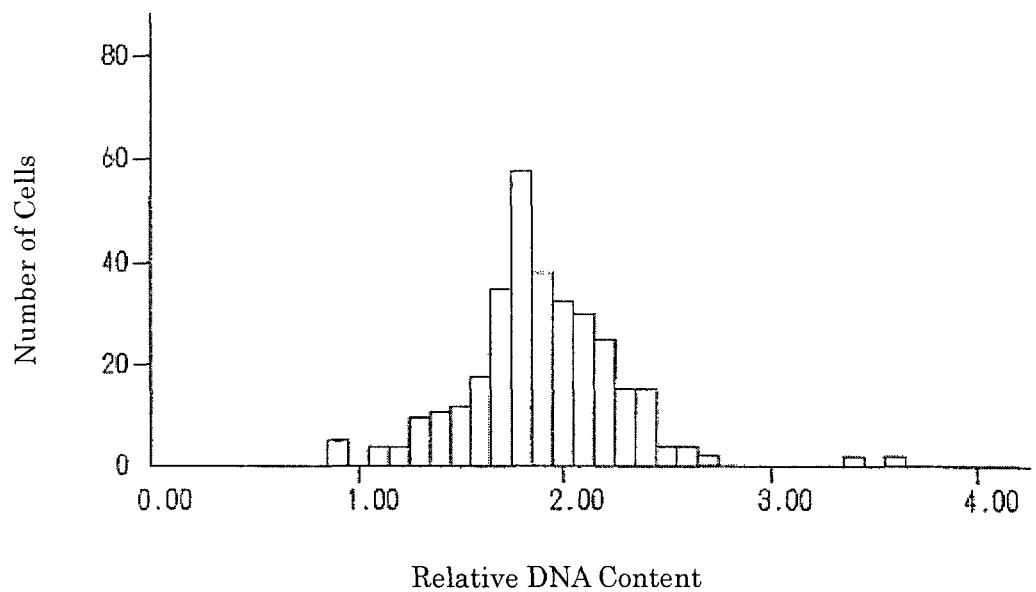
FIG. 6 is a graph showing the relative DNA content of the sperm of an F1 hybrid in the first example, where the corresponding relative DNA content of the parent individual is assumed as two.
Figure 7:
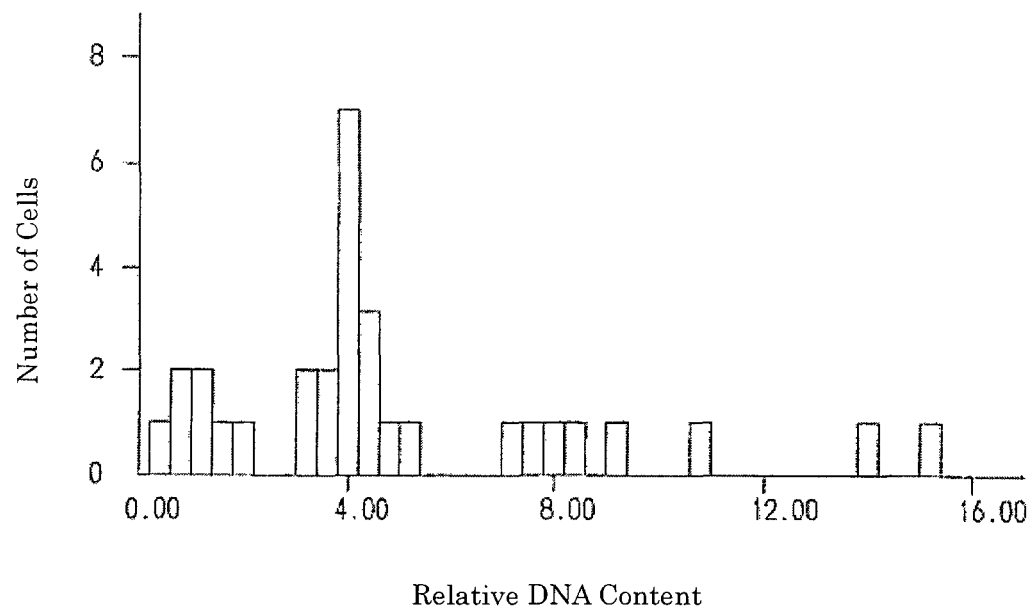
FIG. 7 is a graph showing the relative DNA content of the nucleus of the red blood cell of an F2 hybrid in the first embodiment, where the corresponding relative DNA content of the parent individual is assumed as two.

Six pairs of male and female individuals were each put into a separate concrete aquarium filled with fresh water, into which waterweed was arranged. Five pairs laid eggs. The eggs laid by four pairs had no embryonic body and were determined as unfertilized. In contrast, the eggs laid by the other one pair normally developed and kept growing well even after the hatching. The relative DNA content of the sperm of the male of this pair was approximately two, on the assumption that the relative DNA content of its blood cell was two (see FIG. 6). From this result, that sperm was determined as a nonreductive one. The DNA content distribution of the F2 hybrids had a peak at four (see FIG. 7). Accordingly, they were determined as tetraploids.

The F2 hybrids were all male and had a similar look. The scale transplantation and DNA fingerprint analysis proved that they were genetically identical clones. Their sexual glands were still immature even one year later; whether or not they could be mature in the future could not be confirmed. However, it was later found that some of the three-year fish could ejaculate. Thus, their fertility was confirmed.

The above results can be summarized and interpreted as follows:

Though the hybrids between the goldfish and carp could not create normal gametes, a small number of oocytes in the diplotene stage were developed in the ovaries of the young individuals. In contrast, none of the males had testes that were in the meiotic division stage. These results agree with the conventional knowledge. Among the three-year fish, most of the females were well matured and there was also one male individual capable of ejaculation. The DNA content measurement proved that its sperm was a nonreductive one. The children produced by the crossing among the F1 hybrids were tetraploids, all of which were male individuals and clones. This result suggests that the chromosomes of the reproductive cells before the meiotic division were polyploidized into amphidiploids.

Nonreductive gametes result from the phenomenon that the chromosomes of a reproductive cell are accidentally polyploidized before the meiotic division and the sister chromosomes thereby reproduced behave as homologous chromosomes to enable the pairing. Each of the male and female gametes has one set of the chromosomes of the goldfish and one set of those of the carp, therefore genetically identical to their parents. X and Y sex chromosomes of different species cannot be paired. Therefore, among the male F1 hybrids, the pairing takes place between Xs of the goldfish and between Ys of the carp, and then they are divided. As a result, all the F1 males produce a sperm having XY sex chromosomes. The sex chromosomes of the second (F2) generation are XXXY: two Xs from the goldfish, and X and Y from the carp. The sperm of the male in this generation is either XX or XY. Therefore, the third (F3) and subsequent generations will have males and females by a ratio of 1:1. Thus, a new species that perpetually maintains two sets of goldfish chromosomes and two sets of carp chromosomes is created (the invention of claim 7). Since the genes of the goldfish and carp act as different alleles, inbreeding depression will not take effect even if brother-sister mating is repeated.

Second Example

In this example, a rainbow trout was crossed with a red spotted masu trout to create an amphidiploid according to an embodiment of the invention.

The amphidiploid according to this embodiment of the invention is an XXXY amphidiploid created by producing the first generation of the amphidiploid by suppressing the second cleavage of the cross egg of a hybrid and then fertilizing a reductive egg with a reductive sperm of the first generation. The present inventor has discovered that the polyploidization mechanism that was previously recognized as the "suppression of the first cleavage" for creating a tetraploid is actually the suppression of the "second" cleavage. This fact was made clear by the following experiment:

Fertilized eggs of a rainbow trout, and crossed eggs of a rainbow trout and a red spotted masu trout were cultured at a temperature of 10 degrees Celsius. After five hours fifteen minutes, the eggs were treated with a water pressure of 650 atmospheres for six minutes and then kept at a temperature of 10 degrees Celsius.

Figure 8:
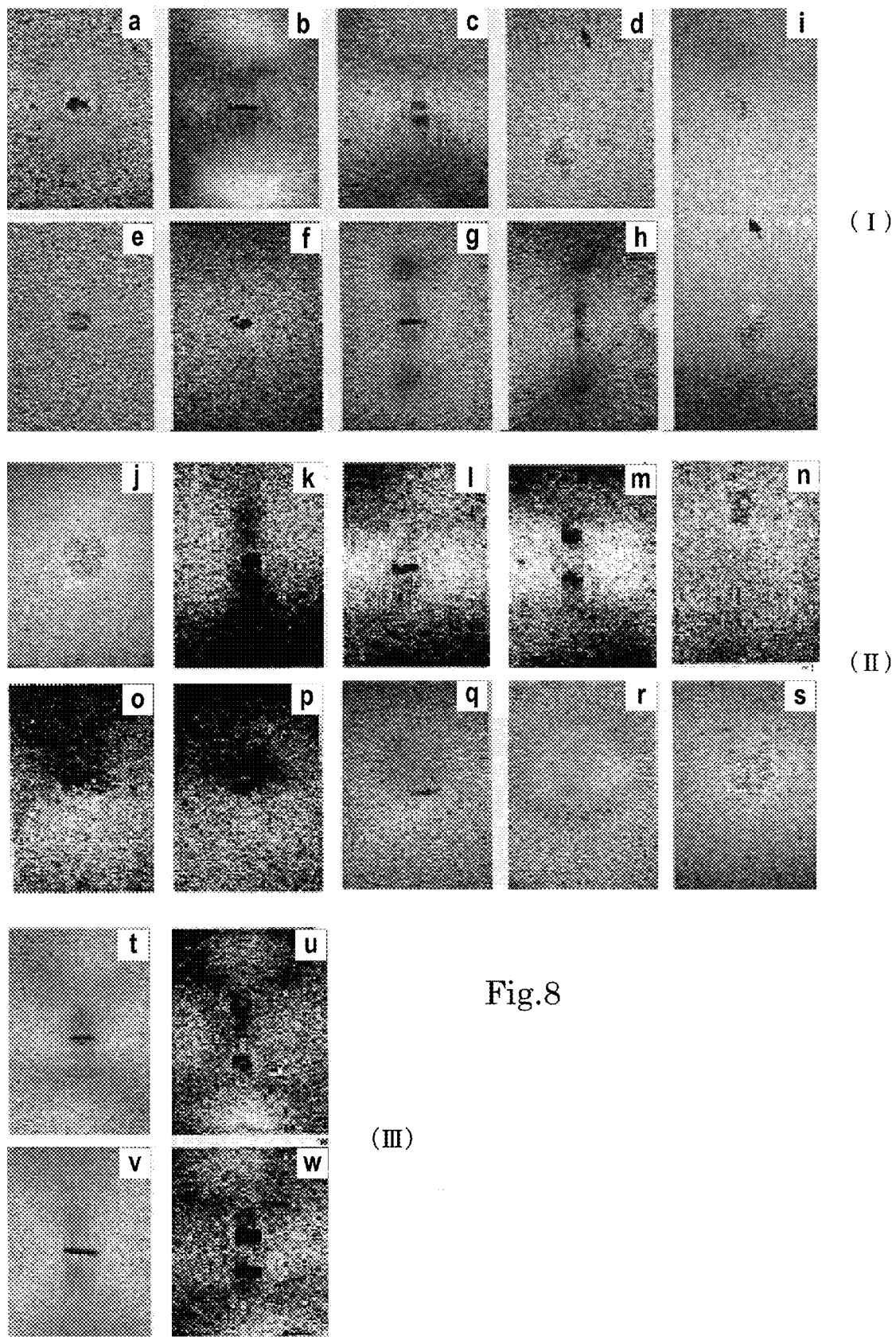
FIG. 8 is a set of pictures showing the nuclear behavior of a water-pressure treatment group in comparison to a control group.

The eggs were fixed immediately before the above process and at specific intervals of time from the process. Using these eggs as the tissue specimens, the behavior of the nucleus was tracked. FIG. 8 shows the result. In this experiment, the fertilized eggs of the rainbow trout are called the control group and the cross eggs of the rainbow trout and the red spotted masu trout are called the treatment group.

In FIG. 8, block I shows the nuclear behavior in the first cell cycle (until the first cleavage is finished), block II shows the nuclear behavior in the second cell cycle (until the control group finishes the second cleavage), and block III shows the nuclear behavior in the third cell cycle. Except picture i, the upper row of each block (a-d in block I, j-n in block II, and t and u in block III) show the nucleus of the control group, and the lower row (e-i in block I, o-s in block II, and v and w in block III) show that of the treatment group.

Nuclear Behavior in the First Cell Cycle (Block I)
Control Group:

Picture a: An image of the nucleus of the control group at the prometaphase, after five hours fifteen minutes from the fertilization. The nuclear membrane has virtually disappeared and the chromosomes can be seen. Asters are recognizable on both sides of the chromosomes. A spindle surrounding the nuclear membrane is also recognizable.

Picture b: An image of the control group at the metaphase, after five hours forty-five minutes from the fertilization. The chromosomes are aligned on the equatorial plate. The spindle is clearly seen.

Picture c: An image of the control group at the anaphase, after six hours fifteen minutes from the fertilization. The chromosomes have started separating toward both poles.

Picture d: An image of the control group at the anaphase, after six hours thirty minutes from the fertilization. The separated chromosomes are forming nuclei. The arrow indicates the image of the first cleavage furrow.

Water-Pressure Treatment Group:

Picture e: An image immediately after the water-pressure treatment was carried out at the phase corresponding to the prometaphase (picture a) of the control group. The aster and centrosome have disappeared.

Picture f: An image after fifteen minutes from the water-pressure treatment. The aster and centrosome have regenerated.

Picture g: An image after thirty minutes from the water-pressure treatment. Thirty minutes later than picture b of the control group, the nucleus is now in the normal metaphase.

Picture h: Subsequent to the metaphase, the nucleus is now in the normal anaphase.

Picture i: Thirty minutes later than picture d of the control group, the nucleus has entered the normal telophase. Two daughter nuclei are formed at both poles, with the first cleavage furrow at the center (indicated by the arrow).

As explained thus far, the spindle firstly disappears (picture e) due to the water-pressure treatment but immediately regenerates. Then, the first cleavage normally starts.

Nuclear Behavior in the Second Cell Cycle (Block II)
Control Group:

Pictures j-n: Images of the nuclei of the control group at the prophase, prometaphase, metaphase, anaphase and telophase in the second cell cycle, respectively. In picture n, the second cleavage furrow can be seen in the lower part of the image.

Water-Pressure Treatment Group:

Picture o: An image of the nucleus of the water-pressure treated embryo at the prophase. The image is approximately the same as the one in picture j.

Picture p: An image of the water-pressure treated embryo at the prometaphase. It has only one aster, which should be normally two.

Picture q: An image of the water-pressure treated embryo at the metaphase. A unipolar spindle is formed since there is only one aster.

Picture r: An image of the water-pressure treated embryo at the anaphase. Since the spindle is unipolar, the chromosomes cannot be separated toward both poles, as opposed to picture m of the control group.

Picture s: An image of the water-pressure treated embryo at the telophase. The chromosomes are formed into one nucleus since they cannot be separated toward both poles. The second cleavage furrow has not been formed, and the embryo still has two cells. The nucleus is larger than the one seen in the telophase image of the control group.

As explained thus far, in the second cell cycle, the nucleus of the water-pressure treatment group cannot create a normal, bipolar spindle but a unipolar one. Therefore, the chromosome separation does not occur and the second cleavage is suppressed. As a result, the chromosomes are polyploidized.

Nuclear Behavior in the Third Cell Cycle (Block III)
Control Group:

Pictures t and u: Images of the control group at the metaphase and anaphase in the third cell cycle.

Water-Pressure Treatment Group:

Pictures v and w: Images of the water-pressure treated nucleus at the metaphase and anaphase. The cleavage normally occurs in the third and subsequent cell cycles. However, the nuclear plate is larger than normal. This means that the chromosomes are polyploidized.

As explained above, in the third cell cycle, the cleavage normally takes places also in the treated embryo. Since the chromosomes are polyploidized, the nuclear plate at the metaphase is larger than normal.

In the results shown in FIG. 8, there is no difference between the fertilized eggs and cross eggs of the rainbow trout in the initial stage of the development. In the control group, after five hours fifteen minutes from the fertilization, or immediately before the treatment was started, most of the eggs were at the prometaphase of the first cleavage. They were at the metaphase after five hours forty-five minutes, the anaphase after six hours fifteen minutes and the telophase after six hours thirty minutes.

In the treatment group, the spindle and aster completely disappeared immediately after the treatment. However, after thirty minutes from the end of the treatment, the spindle regenerated and the embryo entered an apparently normal metaphase. Subsequently, the cleavage normally progressed through the anaphase and telophase, with a delay of about thirty minutes behind the control group.

A remarkable difference between the control and treatment groups was observed in the second cell cycle. The control group entered the metaphase of the second cleavage after nine hours from the fertilization. Within each cell, a bipolar spindle was created and the chromosomes were aligned on the equatorial plate. In contrast, in the treatment group, a unipolar spindle was present within each cell after ten hours. Each spindle was oriented to the center of the embryo, and the chromosomes were aligned at the ends of the spindle fibers, forming an about 120-degree arc. In the anaphase, there was only one nucleus formed, and the cytokinesis did not occur. The nucleus at the anaphase was clearly larger than that of the control group.

To polyploidize chromosomes, a widely adopted method suppresses the cleavage by heat or water pressure. These kinds of physical treatments have been believed to cause the polyploidization by depolymerizing microtubules and making the spindle disappear, thereby preventing the chromosomes from moving toward both poles. Accordingly, this treatment has been called the suppression of the first cleavage.

However, this interpretation is clearly wrong.

Our experiment showed that the spindle regenerated immediately after the water-pressure treatment and, although with some delay, the first cleavage successfully completed. Then, in the second cell cycle, every nucleus in the treatment group created a unipolar spindle inside and every embryo had only one nucleus. Since this nucleus was undoubtedly larger than those of the control group, it was certain that its chromosomes had already been reproduced. In the third cell cycle, the bipolar division occurred in every nucleus. Thus, the cell division returned to the normal mode. All these facts justify the interpretation that the water-pressure treatment performed in the metaphase of the first cleavage actually suppresses the second cleavage. In addition, it has been confirmed that the heat treatment also has basically the same effects as the water-pressure treatment. These results suggest that the water-pressure treatment during the cleavage probably affects the centrosome rather than the spindle.

Referring to FIG. 13, even if the water-pressure or heat treatment is performed in the fourth step, the first cleavage normally progresses. However, a unipolar spindle is created instead of a bipolar one in the sixth step. Since neither the chromosome separation nor the cleavage takes place, each of the two cells will eventually have a tetraploid nucleus inside. This means that the second cleavage is suppressed and a tetraploid is created.

Creation of Amphidiploid of Rainbow Trout and Red Spotted Masu Trout by Water-Pressure Treatment A water-pressure treatment was performed on cross eggs of a rainbow trout and a red spotted masu trout, changing the starting time in steps of fifteen minutes, from four hours forty-five minutes after the fertilization to five hours forty-five minutes. Then, the relationship between the stage of the nucleus at the beginning of the treatment and the polyploidization percentage was investigated. Furthermore, the chromosomes of the 2n-4n mosaic individuals, which appeared in the treatment group, were analyzed to clarify the genome constitution of the 2n cells.

Figure 9:
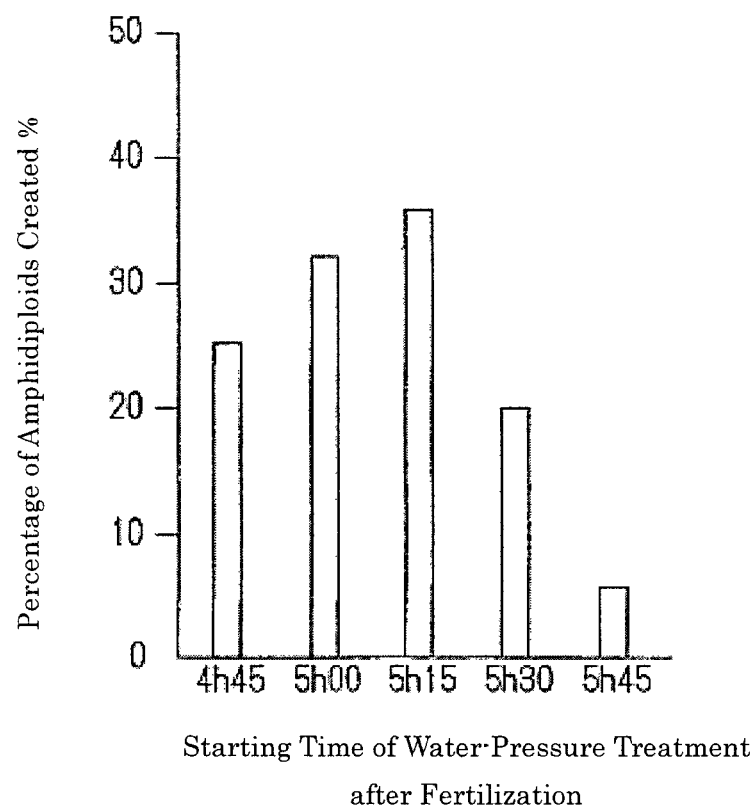
FIG. 9 is a graph showing the relationship between the starting time of the water-pressure treatment and the polyploidization percentage.

FIG. 9 shows the relationship between the treatment-starting time and the polyploidization.

Four hours forty-five minutes corresponds to the prophase of the first cleavage and five hours fifteen minutes corresponds to the prometaphase. The metaphase was from five hours thirty minutes to forty-five minutes. The polyploidization percentage was maximized at five hours fifteen minutes, where approximately forty percent of the eggs used were polyploidized. A karyotype analysis proved those eggs to be homotetraploids. Compared to the eggs whose treatment was started in the prophase, the eggs whose treatment was started in the metaphase had the tendency to have lower percentages of tetraploids.

Figure 10:
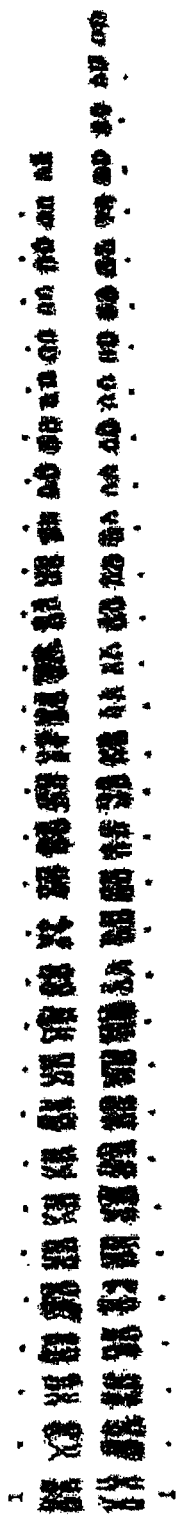
FIG. 10 shows the karyotype of an amphidiploid of a rainbow trout and a red spotted masu trout created in the second example, where the upper row is the chromosomes of a hybrid of the rainbow trout and the red spotted masu trout and the lower low is the chromosomes of the amphidiploid created by suppressing the second cleavage of the cross egg, each row including two sets of the chromosomes of the rainbow trout and two sets of the chromosomes of red spotted masu trout.
Figure 11:
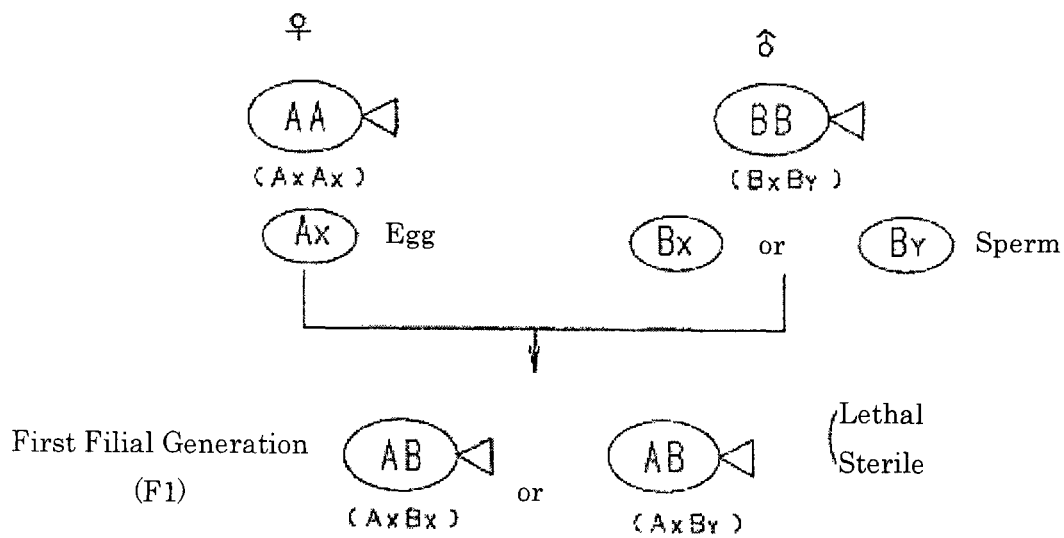
FIG. 11 is a diagram showing the process of creating hybrids.
Figure 12:
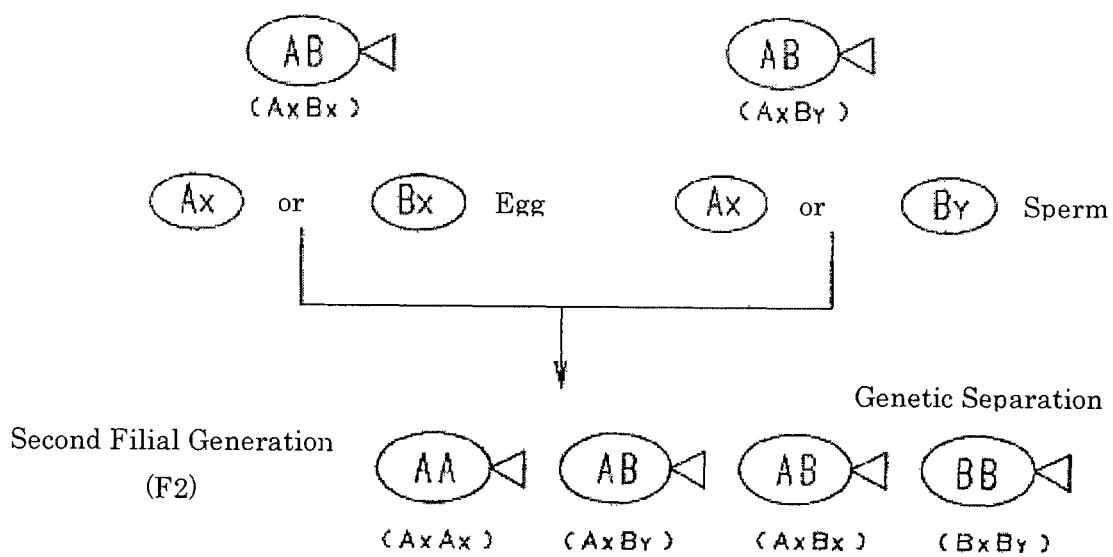
FIG. 12 is a diagram showing the combinations of the chromosomes in the crossing between the individuals of the first filial generation.

FIG. 10 shows the karyotype of the amphidiploid of the rainbow trout and the red spotted masu trout created in the treatment group and that of the hybrid diploid that was not treated.

The relationship between the treatment-starting time and the polyploidization percentage was repeatedly investigated. The conclusion is that the most appropriate phase for starting the treatment is the prometaphase rather than the metaphase. The comparison of the prophase and the metaphase proves that starting the treatment in the prophase provides better results than starting it in the metaphase. If it is true that the polyploidization takes place simply due to the destruction of the spindle by the water-pressure treatment, the metaphase should be also acceptable. The results described thus far concerning the polyploidization mechanism suggest that the physical treatment affects the centrosome rather than the spindle.

A centrosome consists of two centrioles. In advance of the cell division, the two centrioles separate from each other, and then each of them creates its copy in a budding manner. The formation of the daughter centriole is known to continue until the metaphase of the cell division. The centriole is a kind of microtubule made of gamma tubulin. It can be assumed that a matured centriole is scarcely affected by the water-pressure treatment, whereas a centriole that emerges during the reproduction process is easily affected. This assumption well explains the relationship between the treatment-starting time and the polyploidization. At the initial phase of the reproduction of the daughter centriole, the water-pressure treatment is less effective because a centriole destroyed by the water-pressure can regenerate after the treatment. However, after the treatment has progressed to a certain extent, the regeneration is probably impossible. As a result, the first cleavage will be completed with only one centriole.

At the metaphase and subsequent phases of the cell division, the water-pressure is not effective since the centriole is fully reproduced. This is probably the reason for the decrease of the polyploidization percentage. A centriole that had its copy destroyed and therefore could not reproduce itself during the reproduction process will again reproduce a daughter centriole during the second cell cycle and form a new, full-grown centriole. This is probably the reason why the unipolar spindle is created.

The amphidiploid having fertile XXXY sex chromosomes according to the present invention includes any amphidiploid created by the techniques explained thus far. Examples include: an amphidiploid created by fertilizing a nonreductive egg $A_X A_X B_X$ of a fertile hybrid triploid of an aquatic animal with a reductive sperm $B_Y$ of an aquatic animal having BB chromosomes; an amphidiploid created by the steps of fertilizing an egg $A_X A_X$ of an aquatic animal having AA chromosomes with a sperm $B_X$ or $B_Y$ of an aquatic animal having BB chromosomes, then fertilizing the egg with a sperm $B_Y$ or $B_X$ by microinjection, and suppressing the release of the second polar body; and an amphidiploid created by fertilizing an egg $A_X A_X$ with a sperm $B_X B_Y$, each produced by autotetraploids AAAA and BBBB.

The techniques described in the previous examples, which were all related to fish, can be similarly applied to shellfish, Crustacea and similar aquatic animals commonly found in the aquaculture and propagation industries. In general, aquatic animals produce an enormous amount of eggs per individual and thereby provide a large number of populations from which intended individuals are to be selected. Therefore, the desired variation of fertilized eggs or children can be efficiently produced by one and the same technique. Accordingly, the technique or idea that can be applied to fish to create amphidiploids is also applicable to other kinds of aquatic animals.

The following two papers are hereby referred to as the documents demonstrating that chromosome operations can be effectively performed not only on fish but also on shellfish or Crustacea:

(1) Guo, X. and Allen, Jr. S. R., 1994, "Viable tetraploids in the Pacific oyster (*Crassostrea gigas* Thunberg) produced by inhibiting polar body 1 in eggs from triploids", Molecular Marine Biology Biotechnology, 3, 42-50.

(2) Li, F. Xiange, J., Zou, L., Wu, C. and Zhang, X., 2003, "Optimization of triploid induction by heat shock in Chinese shrimp *Fenneropenaeus chinensis*", Aquaculture, 219, 221-231.

The amphidiploid according to the present invention has a chromosome constitution that has been neither found in the natural world nor theoretically predicted. The present inventor has succeeded in its creation. This invention ensures a stable supply of the amphidiploid in the next and subsequent generations by natural crossbreeding. The utility value of this technique is immeasurable, particularly in the field of aquaculture.

What is claimed is:

1. A method of breeding a second hybrid (F2) generation which is a male amphidiploid fish having fertile XXXY sex chromosomes and a hybrid between a female fish (A) and a male fish (B) comprising:
   producing the F2 generation which is the male amphidiploid fish having fertile AxAxBxBy sex chromosomes,
   said F2 generation produced by fertilizing an egg AxBx with a sperm AxBy, both produced by a first hybrid (F1) generation which are an amphidiploid female fish having AxAxBxBx sex chromosomes and an amphidiploid male fish having AxAxByBy sex chromosomes,
   said F1 generation produced by suppressing a second cleavage of a cross-breeding egg AxBx and AxBy cross breeding a diploid female fish having the genome AxAx with a diploid male fish having the genome BxBy, wherein sperm of the male F2 amphidiploid fish is either XX or XY, thereby the third hybrid (F3) generation and subsequent generations having males and females by a ratio of 1:1.

* * * * *